US012334209B2

(12) United States Patent
Yoo et al.

(10) Patent No.: US 12,334,209 B2
(45) Date of Patent: Jun. 17, 2025

(54) DEVICE AND METHOD FOR PROVIDING REMOTE TREATMENT SERVICE

(71) Applicant: Samsung Electronics Co., Ltd., Suwon-si (KR)

(72) Inventors: Sung Yoo, Suwon-si (KR); Jeongmin Park, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 17/951,736

(22) Filed: Sep. 23, 2022

(65) Prior Publication Data

US 2023/0112728 A1 Apr. 13, 2023

Related U.S. Application Data

(63) Continuation of application No. PCT/KR2022/012865, filed on Aug. 29, 2022.

(30) Foreign Application Priority Data

Oct. 8, 2021 (KR) .................. 10-2021-0134284
Nov. 15, 2021 (KR) .................. 10-2021-0157030

(51) Int. Cl.
*G16H 20/70* (2018.01)
*A61B 5/00* (2006.01)
(Continued)

(52) U.S. Cl.
CPC ............. *G16H 20/70* (2018.01); *A61B 5/486* (2013.01); *G16H 40/63* (2018.01); *A61B 5/16* (2013.01);
(Continued)

(58) Field of Classification Search
CPC ........ G16H 20/70; G16H 40/63; A61B 5/486; A61B 5/16; A61B 5/162; A61N 1/37247; A61N 1/36135; A61M 21/00
See application file for complete search history.

(56) References Cited

U.S. PATENT DOCUMENTS 5,807,114 A  9/1998 Hodges et al.
5,911,581 A * 6/1999 Reynolds .................. G09B 7/04
434/236

(Continued)

FOREIGN PATENT DOCUMENTS

CN 203480511 U 3/2014
CN 108461126 A 8/2018
(Continued)

OTHER PUBLICATIONS

International Search Report dated Nov. 30, 2022 issued in the corresponding PCT application No. PCT/KR2022/012865.
(Continued)

*Primary Examiner* — Jack Yip
(74) *Attorney, Agent, or Firm* — Jefferson IP Law, LLP

(57) ABSTRACT

A method of operating a server for remote treatment is provided. The method includes transmitting, to an electronic device of a user, a treatment package corresponding to the treatment request among a plurality of treatment packages, and based on the treatment package, based on the authentication information, receiving at least one of biometric information of the user and feedback information of the user, determining whether to continue the treatment package based on at least one of the biometric information and the feedback information, transmitting, to the electronic device, a control signal for adjusting an intensity of the treatment image based on at least one of the biometric information and the feedback information according to a determination to continue the treatment package, and transmitting, to the (Continued)

electronic device, a control signal for discontinuing the display of the treatment image according to a determination to discontinue the treatment package.

23 Claims, 11 Drawing Sheets

(51) Int. Cl.
| | | |
|---|---|---|
| *G16H 40/63* | (2018.01) | |
| *A61B 5/16* | (2006.01) | |
| *A61M 21/00* | (2006.01) | |
| *A61N 1/36* | (2006.01) | |
| *A61N 1/372* | (2006.01) | |

(52) U.S. Cl.
CPC .............. *A61B 5/162* (2013.01); *A61M 21/00* (2013.01); *A61N 1/36135* (2013.01); *A61N 1/37247* (2013.01)

(56) References Cited

U.S. PATENT DOCUMENTS

| | | | |
|---|---|---|---|
| 6,012,926 A | 1/2000 | Hodges et al. | |
| 6,425,764 B1 | 7/2002 | Lamson | |
| 6,435,878 B1* | 8/2002 | Reynolds | A61B 5/162 |
| | | | 434/236 |
| 9,620,030 B2* | 4/2017 | Peterson | G09B 19/00 |
| 10,901,509 B2 | 1/2021 | Aimone et al. | |
| 11,049,326 B2 | 6/2021 | Samec et al. | |
| 2005/0187436 A1* | 8/2005 | Doniger | A61B 5/16 |
| | | | 128/920 |
| 2007/0166675 A1* | 7/2007 | Atkins | G09B 7/04 |
| | | | 434/236 |
| 2007/0293732 A1* | 12/2007 | Delahunt | G09B 7/02 |
| | | | 709/213 |
| 2011/0245633 A1* | 10/2011 | Goldberg | A61B 5/165 |
| | | | 600/323 |
| 2014/0074180 A1* | 3/2014 | Heldman | A61N 1/36067 |
| | | | 607/45 |
| 2014/0370479 A1* | 12/2014 | Gazzaley | A61B 5/168 |
| | | | 434/322 |
| 2015/0126899 A1* | 5/2015 | Ghajar | A61B 5/4064 |
| | | | 434/236 |
| 2017/0053078 A1* | 2/2017 | Lanzel | A61B 5/0205 |
| 2020/0302825 A1* | 9/2020 | Sachs | G09B 5/02 |
| 2021/0065571 A1 | 3/2021 | Javanbakht | |

FOREIGN PATENT DOCUMENTS

| | | |
|---|---|---|
| CN | 109949896 A | 6/2019 |
| CN | 111785352 A | 10/2020 |
| KR | 10-1793426 B1 | 11/2017 |
| KR | 10-2018-0095148 A | 8/2018 |
| KR | 10-2018-0097947 A | 9/2018 |
| KR | 10-1928415 B1 | 12/2018 |
| KR | 10-2019-0015907 A | 2/2019 |
| KR | 10-1945452 B1 | 2/2019 |
| KR | 10-2019-0061826 A | 6/2019 |
| KR | 10-2165592 B1 | 10/2020 |
| KR | 10-2170379 B1 | 10/2020 |
| KR | 10-2021-0024971 A | 3/2021 |
| KR | 10-2241829 B1 | 4/2021 |
| WO | 2021/009412 A1 | 1/2021 |

OTHER PUBLICATIONS

Extended European Search Report dated Oct. 11, 2024 issued in European Patent Application No. 22878726.3.

* cited by examiner

FIG. 4

Table 401 (410: -3/-2; 420: Event; 430: +1/+2/+3/+4):

| | -3 | -2 | Event | +1 | +2 | +3 | +4 |
|---|---|---|---|---|---|---|---|
| Heart rate | 80 | 80 | 150 | 145 | 146 | 135 | 130 |
| Blood pressure | 120/80 | 120/80 | 150/90 | 145/100 | 140/90 | 139/90 | 126/80 |
| Stress index | 2/10 | 2/10 | 8/10 | 8 | 7 | 7 | 6 |

Table 400 (450: Session 2; 460: Session 5):

| | Normal | Session 1 | Session 2 | Session 3 | Session 4 | Session 5 | Session 6 | Session 7 |
|---|---|---|---|---|---|---|---|---|
| Heart rate (471) | 80 | 130 | 150 | 110 | 100 | 120 | 90 | 100 |
| Blood pressure (472) | 120/80 | 145/100 | 150/90 | 130/82 | 132/90 | 128/79 | 125/40 | 123/80 |
| Stress index (473) | 2/10 | 7 | 8 | 5 | 3 | 5 | 3 | 3 |
| Treatment intensity (474) | | 6 | 9 | 4 | 2 | 6 | 2 | 2 |

| | 541 | 542 | 543 | 544 | 545 | 546 | 547 |
|---|---|---|---|---|---|---|---|
| | Date | Treatment intensity | Tolerability | Symptom | Heart rate | Blood pressure | Stress index |
| | 5/2: | 2 | O | Moderate anxiety | 80 | 125/92 | Mid |
| 510 | 5/3: | 2 | O | Mild anxiety | 90 | 125/92 | Mid |
| 520 | 5/4: | 3 | O | Hyperventilation | 110 | 125/92 | Mid |
| | 5/5: | 2 | O | Minimum anxiety | 90 | 125/92 | Mid |
| | 5/6: | 3 | O | No anxiety | 70 | 125/92 | Mid |
| 530 | 5/7: | 4 | X | Hyperventilation | 120 | 158/96 | High |
| | 5/8: | Skipped | | | | | |
| | 5/8: | 3 | O | No symptoms | 80 | 125/92 | Mid |

FIG. 5

DEVICE AND METHOD FOR PROVIDING REMOTE TREATMENT SERVICE

CROSS-REFERENCE TO RELATED APPLICATION(S)

This application is a continuation application, claiming priority under § 365(c), of an International application No. PCT/KR2022/012865, filed on Aug. 29, 2022, which is based on and claims the benefit of a Korean patent application number 10-2021-0134284, filed on Oct. 8, 2021, in the Korean Intellectual Property Office, and of a Korean patent application number 10-2021-0157030, filed on Nov. 15, 2021, in the Korean Intellectual Property Office, the disclosure of each of which is incorporated by reference herein in its entirety.

BACKGROUND

1. Field

The disclosure relates to a method and device for providing a remote treatment service.

2. Description of Related Art

Currently people have various types of mental illnesses and receive aid from medical professionals to treat them. Among various mental illnesses, a certain phobia may refer to a fear or anxiety that is immediately evoked in relation to a specific object or a situation. A progressive exposure treatment may be used to treat mental illnesses, such as a certain phobia.

The development of information and communication technology (ICT) allows people with a mental illness to be treated remotely for the mental illness, using the progressive exposure treatment without visiting a medical institution. Therefore, interest in remote treatment technology is gradually on the rise.

The above information is presented as background information only to assist with an understanding of the disclosure. No determination has been made, and no assertion is made, as to whether any of the above might be applicable as prior art with regard to the disclosure.

SUMMARY

Patients may visit a medical institution and use medical facilities and systems in the medical institution to treat their mental illness. Unfortunately, differences in medical facilities and systems by medical institutions may cause spatial and physical restrictions in treatment. In addition, there may be a time constraint since a patient has to make an appointment with a medical institution and personally visit the medical institution.

Aspects of the disclosure are to address at least the above-mentioned problems and/or disadvantages and to provide at least the advantages described below. Accordingly, an aspect of the disclosure is to provide a remote treatment service to users via various types of electronic devices.

Another aspect of the disclosure is to provide a user receiving a remote treatment service in which some procedures are automated, using treatment data.

Another aspect of the disclosure is to provide patients being remotely treated for their mental illness anytime and anywhere via a treatment package suitable for their mental illness as a server has treatment packages corresponding to various mental illnesses.

Additional aspects will be set forth in part in the description which follows and, in part, will be apparent from the description, or may be learned by practice of the presented embodiments.

In accordance with an aspect of the disclosure, a method of operating a server for remote treatment is provided. The method includes receiving a treatment request including a user's authentication information, transmitting, to an electronic device of the user, a treatment package corresponding to the treatment request among a plurality of treatment packages based on the authentication information, wherein a treatment mage at a predetermined intensity is output based on the treatment package using a display of the electronic device, receiving at least one of biometric information of the user and feedback information of the user to monitor the user's response to the treatment image, determining whether to continue the treatment package based on at least one of the biometric information and the feedback information, transmitting, to the electronic device, a signal for controlling the intensity of the treatment image based on at least one of the biometric information and the feedback information according to a determination to continue the treatment package, and transmitting, to the electronic device, a signal for discontinuing the display of the treatment image according to a determination to discontinue the treatment package.

In accordance with another aspect of the disclosure, a method of operating a user terminal for remote treatment is provided. The method includes transmitting a treatment request including a user's authentication information, receiving a treatment package corresponding to the treatment request from among a plurality of treatment packages based on the authentication information, outputting a treatment image at a predetermined intensity on a display, or a display of a wearable device, based on the treatment package, receiving at least one of biometric information of the user and feedback information of the user to monitor the user's response to the treatment image, determining whether to continue the treatment package based on at least one of the biometric information and the feedback information, adjusting an intensity of the treatment image based on at least one of the biometric information and the feedback information once it is determined to continue the treatment package, and discontinuing the display of the treatment image and executing a biofeedback package once it is determined to discontinue the treatment package.

A method of providing a remote treatment service, according to one embodiment, may allow users to receive a treatment service without temporal, spatial, or physical limitations.

The method of providing a remote treatment service, according to another embodiment, may configure various environments necessary for a progressive exposure treatment, using augmented reality or virtual reality technology, and may provide a treatment service for a user in various environments.

The method of providing a remote treatment service, according to another embodiment, may provide a remote treatment service for various mental illnesses.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 4 is a diagram illustrating prior signs according to an embodiment of the disclosure;

FIG. 5 is a diagram illustrating an adjustment of treatment intensity according to an embodiment of the disclosure;

Throughout the drawings, it should be noted that like reference numbers are used to depict the same or similar elements, features, and structures.

DETAILED DESCRIPTION

Figure 1:
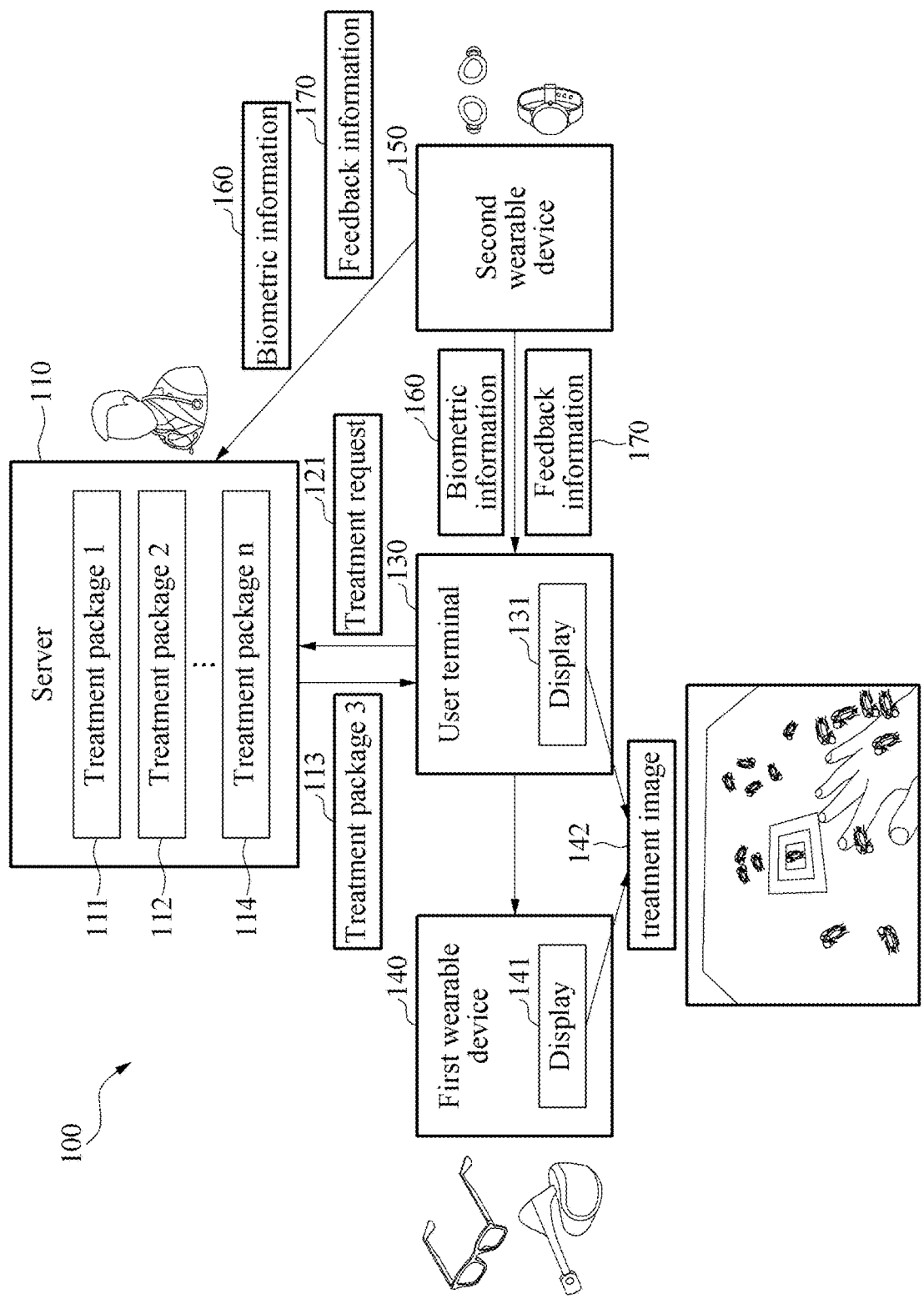
FIG. 1 illustrates a method of providing a remote treatment service, according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Although terms of "first" or "second" are used to explain various components, the components are not limited to the terms. These terms should be used only to distinguish one component from another component. For example, a "first" component may be referred to as a "second" component, or similarly, and the "second" component may be referred to as the "first" component within the scope of the right according to the concept of the disclosure.

It should be noted that if it is described that one component is "connected", "coupled", or "joined" to another component, a third component may be "connected", "coupled", and "joined" between the first and second components, although the first component may be directly connected, coupled, or joined to the second component. On the contrary, it should be noted that if it is described that one component is "directly connected", "directly coupled", or "directly joined" to another component, a third component may be absent. Expressions describing a relationship between components, for example, "between", directly between", or "directly neighboring", etc., should be interpreted to be alike.

It should be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined, all terms used herein including technical or scientific terms have the same meaning as commonly understood by one of ordinary skill in the art to which examples belong. Terms, such as those defined in commonly used dictionaries, are to be interpreted as having a meaning that is consistent with their meaning in the context of the relevant art, and are not to be interpreted in an idealized or overly formal sense unless expressly so defined herein.

Hereinafter, examples will be described in detail with reference to the accompanying drawings. In the drawings, like reference numerals are used for like elements.

FIG. 1 illustrates a method of providing a remote treatment service, according to an embodiment of the disclosure.

Referring to FIG. 1, illustrates a system 100 including a server 110, a plurality of treatment packages 111, 112, 113, and 114, a treatment request 121, a user terminal 130, a display 131 of the user terminal 130, a first wearable device 140, a display 141 of the first wearable device 140, a second wearable device 150, a treatment image 142, biometric information 160, and feedback information 170.

According to one embodiment, the server 110 may receive the treatment request 121 including a user's authentication information. The server 110 according to a second embodiment may be a server for providing a treatment service. The server 110 for providing the treatment service may be a server 1008 in FIG. 9. According to another embodiment, the user's authentication information may include information for providing a treatment package only for a user corresponding to the treatment package. A user's medical-related data may be sensitive personal information. To protect personal information, the server 110 may provide a treatment package only to an authenticated user. The server 110 may transmit the treatment package corresponding to a user only to the user who passes a user authentication process. The treatment package according to another embodiment may be installed on the user terminal 130 solely based on a prescription of a medical professional. For example, the server 110 may guide a user to install the treatment package only when the user performs the user authentication via an installation link to prevent many and unspecified people from accessing the server 110. For example, the treatment package may be set to input a designated password or to be installed only in a designated electronic device.

According to another embodiment, the treatment request 121 may include a request for treating a mental illness with which a user is diagnosed, using an electronic device. The treatment request 121 according to another embodiment may include at least one of information about a mental illness (e.g., a specific phobia) with which the user of the treatment request 121 is diagnosed by a medical professional, and information about a treatment package (e.g., a specific phobia treatment package), which corresponds to a mental illness and is prescribed to the user by a medical professional. The server 110 may transmit a treatment package suitable for a user based on the information of their mental illness and the treatment package included in the treatment request. The server 110 according to another embodiment may store a plurality of treatment packages respectively corresponding to various types of mental illnesses. The server 110 may have a treatment package library, which includes a plurality of treatment packages. When a new mental illness according to another embodiment is discovered, a treatment package corresponding to the new mental illness may be added to the treatment package library, and such an addition allows the server 110 to immediately provide a treatment service for the new mental illness to a user.

According to another embodiment, the server 110 may transmit, to a user's electronic device, a treatment package corresponding to the treatment request 121 among the plurality of treatment packages 111, 112, 113, and 114, based on authentication information. According to another embodiment, the server 110 may receive the treatment request 121 from the user terminal 130. The server 110 may transmit the third treatment package 113 corresponding to the treatment request 121 to the user terminal 130 based on the authentication information. The third treatment package 113 may be, for example, a package including data for the treatment of a specific phobia.

The server 110 according to another embodiment may receive the treatment request 121 from the first wearable device 140 or the second wearable device 150. The server 110 may transmit the third treatment package 113 corresponding to the treatment request 121 to the user terminal 130, the first wearable device 140, and/or the second wearable device 150, based on the authentication information. However, the foregoing is merely an example, and the server 110 may receive the treatment request 121 from various types of electronic devices and may transmit a treatment package corresponding to the treatment request 121 to various types of electronic devices.

Figure 9:
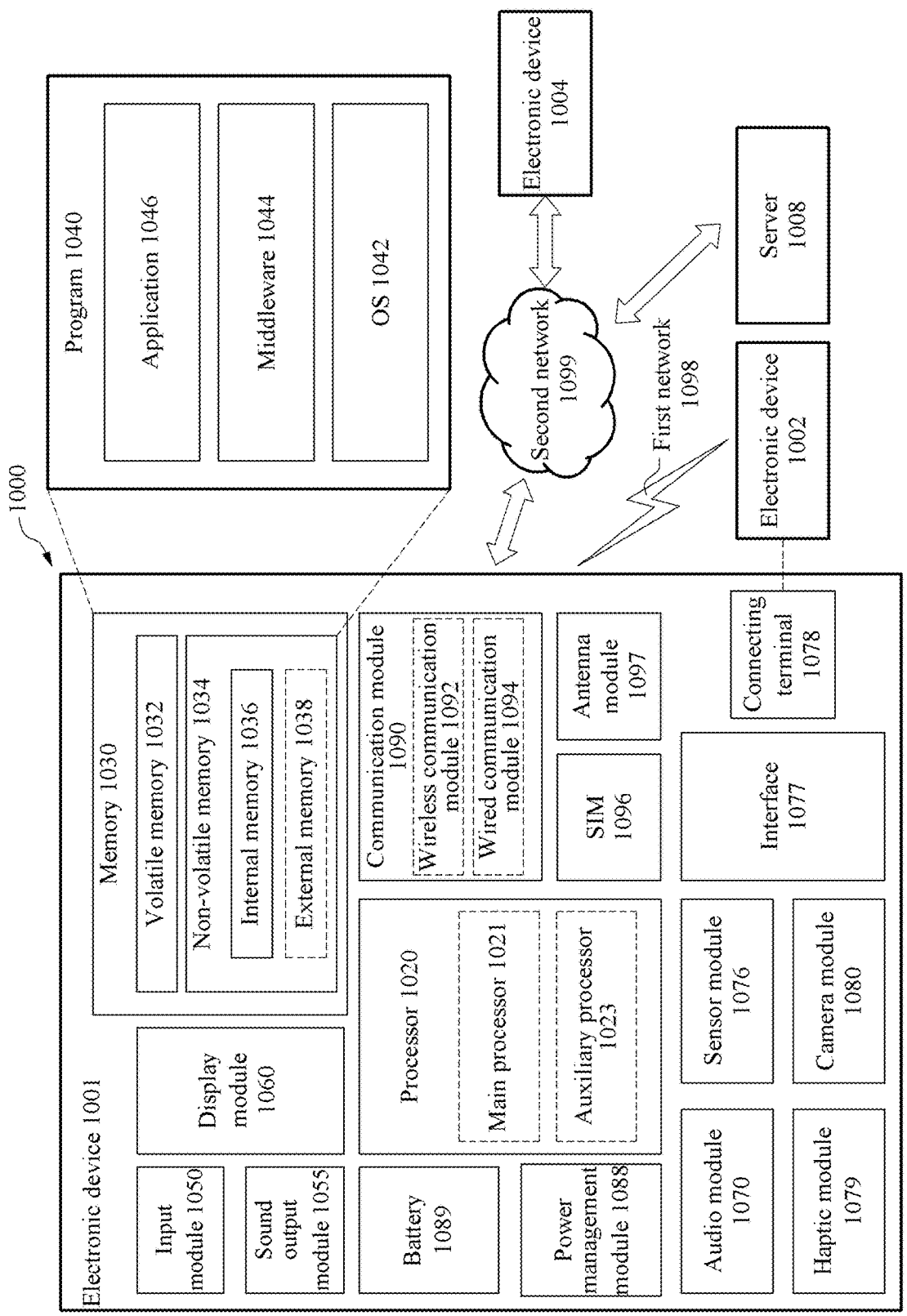
FIG. 9 is a block diagram illustrating an electronic device in a network environment according to an embodiment of the disclosure.

According to another embodiment, the treatment image 142 at a predetermined intensity may be output on a display of an electronic device, based on a treatment package. According to another embodiment, an electronic device may include the user terminal 130 and/or a wearable device. The electronic device according to another embodiment may include at least one wearable device mounted on a part of a user's body and the user terminal 130 that transmits and receives data to and from the wearable device. The wearable device may include, for example, a smart view, smart glasses, a smart belt, smart clothing, and/or a head mounted display. The user terminal 130 may include, for example, mobile devices, desktops, and/or laptops. The wearable device and the user terminal 130 described herein are merely examples, and the disclosure is not limited thereto. As illustrated in FIG. 9, the electronic device may include various types of devices having computing capabilities other than a mobile device and a wearable device.

A treatment package according to another embodiment may include the treatment image 142 at a predetermined intensity. The treatment package may be installed on the user terminal 130 to allow the treatment image 142 at a predetermined intensity to be output on a display. In addition, the user terminal 130 may transmit the treatment image 142 to a wearable device to output the treatment image 142 on a display of the wearable device. According to another embodiment, the treatment image 142 at a predetermined intensity may be stored in the server 110. Accordingly, the treatment image 142 at a predetermined intensity may be provided in a streaming form on the web, based on a signal from the user terminal 130 or the wearable device.

According to another embodiment, the wearable device may include at least one of the first wearable device 140 positioned on the user's head and the second wearable device 150 positioned on the user's body part other than the head. The first wearable device 140 may include a wearable device for displaying the treatment image 142 to a user. The first wearable device 140 may include a wearable device that collects the biometric information 160 including an electroencephalogram (EEG) signal. The second wearable device 150 according to another embodiment may include a wearable device for collecting the biometric information 160. The second wearable device 150 may include a wearable device that is attached to a user's hand, wrist, arm, foot, ankle, knee, thigh, waist, and/or torso to collect their body information.

According to another embodiment, the treatment image 142 may be output on the display 131 of the user terminal 130. According to another embodiment, the treatment image 142 may be output on the display 141 of the first wearable device 140. The first wearable device 140 according to another embodiment may include a device that outputs augmented reality and/or virtual reality on a display. The display may allow a user to view the treatment image 142 as a realistic image through the first wearable device 140.

According to another embodiment, the server 110 may receive at least one of the biometric information 160 of the user and the feedback information 170 of the user to monitor the user's response to the treatment image 142.

According to another embodiment, the biometric information 160 may include information for identifying the user's current physical state. The biometric information 160 of the user may include at least one of a heart rate, an electrocardiogram, a respiratory rate (RR), a blood pressure, a body temperature, a blood oxygen saturation, and a lactate level. According to another embodiment, the biometric information 160 may include information obtained from the second wearable device 150. For example, the second wearable device 150 may include a wearable device worn on a part of the user's body.

According to another embodiment, the feedback information 170 of the user may include subjective information obtained from the user who viewed the treatment image 142. The biometric information 160 may be objective information of the user's reaction to the treatment image 142. The feedback information 170 may be subjective information of the user's reaction to the treatment image 142. The feedback information 170 may, for example, include the user's answer obtained through a survey. For example, a question may be "How much fear did you feel from the treatment image? Please express it as a number between 1-10." In response to the question, the user may answer 9 when they feel a lot of fear. In this case, 9, which is the user's answer to the question, may be included in the feedback information 170.

According to another embodiment, the server 110 may determine whether to continue a treatment package based on at least one of the biometric information 160 and the feedback information 170.

According to another embodiment, the server 110 may determine that the user continues the treatment package. The server 110 may transmit a control signal for adjusting the intensity of the treatment image 142 to an electronic device, based on at least one of the biometric information 160 and the feedback information 170. A specific method of adjusting treatment intensity is described herein with reference to FIGS. 5, 8A, 8B, and 8C in detail.

According to another embodiment, the server 110 may transmit a control signal for discontinuing the display of the treatment image 142 to the electronic device, according to a determination that the treatment package is to be discontinued. A detailed description of the process of discontinuing the treatment package is described herein with reference to FIG. 2 in detail.

Figure 2:
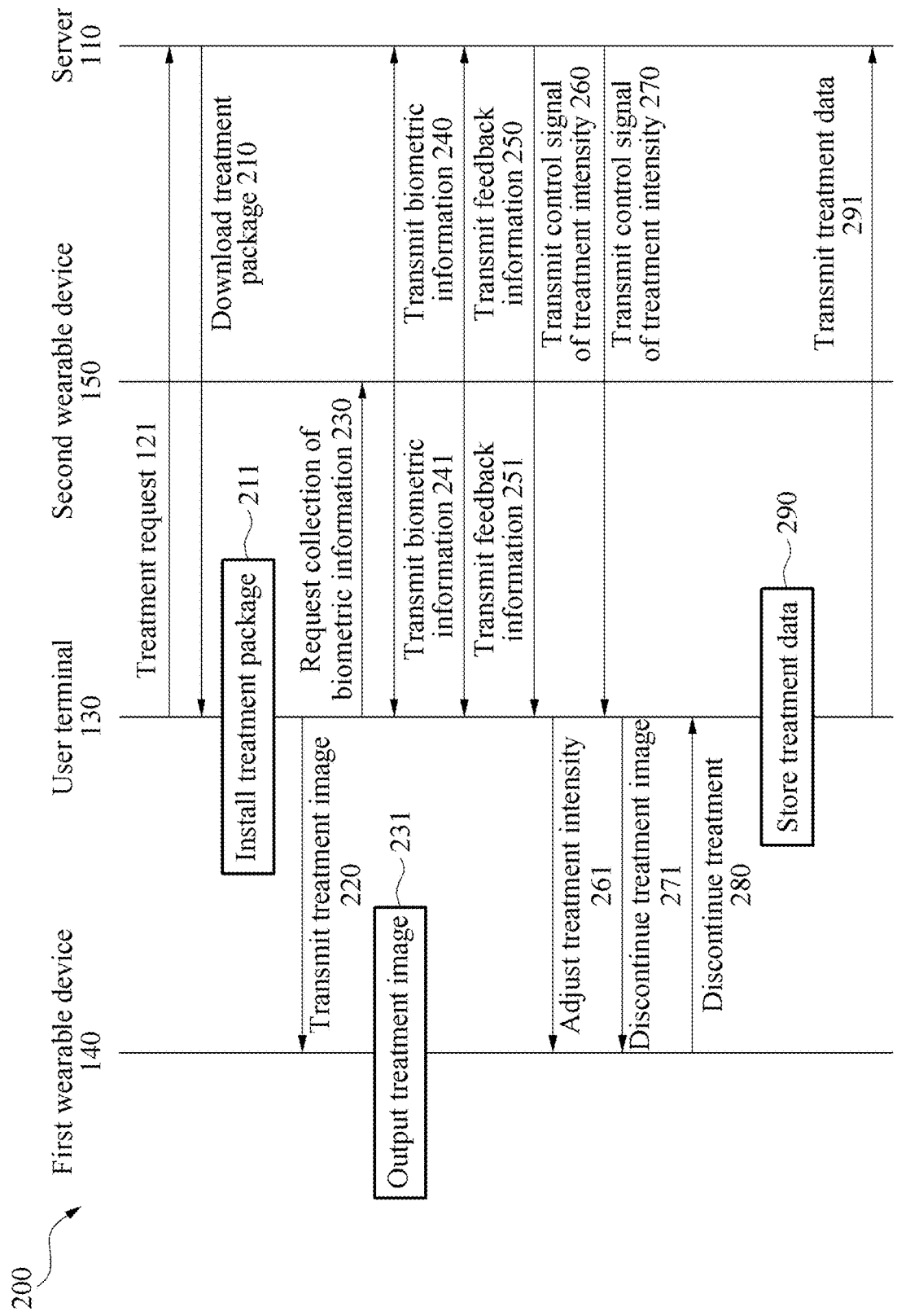
FIG. 2 is a flowchart illustrating a method of providing a remote treatment service according to an embodiment of the disclosure.

FIG. 2 is a flowchart illustrating a method of providing a remote treatment service, according to an embodiment of the disclosure.

Referring to FIG. 2, according to one embodiment, in a method 200, a server 110 may receive a treatment request 121 from a user terminal 130. The server 110 may transmit a treatment package corresponding to the treatment request 121 to the user terminal 130, based on authentication information. The user terminal 130 may download the treatment package from the server 110 in operation 210. The user terminal 130 may install the treatment package in operation 211. The treatment package according to a second embodiment may include software capable of providing a treatment service to a user. For example, when the treatment package is installed on the user terminal 130, a treatment service may be provided, using a program (e.g., an application) installed on the user terminal 130. According to an example, the treatment package may be provided online without being installed on the user terminal 130. That is, the user may be provided with the treatment service online without installing a treatment package in the user terminal 130. For example, the user may view a treatment image 142 on a display by an online stream. As another example, the user may view the treatment image 142 in the form of downloaded media on the display.

The user terminal 130 according to another embodiment may output the treatment image 142 included in the treatment package on a display of the user terminal 130. Therefore, the user may view the treatment image 142 on a display of the user terminal 130 without using a wearable device. That is, a user may receive a treatment service even without a wearable device, using the user terminal 130.

According to another embodiment, the user terminal 130 may transmit the treatment image 142 included in a treatment package to the first wearable device 140 in operation 220. The first wearable device 140 may receive the treatment image 142 and output the treatment image 142 on the display of the first wearable device 140.

According to another embodiment, in order to monitor a user's reaction, the server 110 may receive biometric information 160 and/or feedback information 170 from a second wearable device 150. That is, the second wearable device 150 may transmit the biometric information 160 to the server 110 in operation 240 and further transmit the feedback information 170 to the server 110 in operation 250. The second wearable device 150 according to another embodiment may transmit the biometric information 160 and/or the feedback information 170 to the user terminal 130. The user terminal 130 may transmit, to the second wearable device 150, a request for collecting the biometric information 160 in operation 230 in order to receive the biometric information 160 from the second wearable device 150. Upon receipt of the request, the second wearable device 150 may transmit the biometric information 160 to the user terminal 130 in operation 241. The second wearable device 150 according to another embodiment may transmit the feedback information 170 to the user terminal 130 in operation 251. This may allow the user terminal 130 to adjust treatment intensity without a control signal of the server 110, based on the received biometric information 160 and/or feedback information 170. The server 110 may receive the biometric information 160 and/or the feedback information 170 from the user terminal 130 and/or the first wearable device 140 as well as the second wearable device 150.

The server 110 according to another embodiment may transmit a treatment intensity control signal to the user terminal 130 in operation 260, based on the biometric information 160 and/or the feedback information 170. The server 110 may receive the biometric information 160 and/or the feedback information 170 from the user terminal 130. The server 110 may transmit a treatment intensity control signal to the user terminal 130 in operation 260, based on the biometric information 160 and/or the feedback information 170 received from the user terminal 130. That is, the server 110 may adjust the intensity of the treatment image 142 through communications with the user terminal 130. Hereinafter, another embodiment of adjusting intensity of the treatment image 142 is disclosed.

The server 110 according to another embodiment may control the intensity of the treatment image 142 based on diagnosis information that a medical professional generates on the basis of the biometric information 160 and the feedback information 170 during a predetermined period. Based on the biometric information 160 and the user's feedback information 170 received by the server 110, a medical professional (e.g., a doctor) may adjust treatment intensity. Diagnostic information according to another embodiment may include information for setting the intensity of the treatment image 142 suitable for a user, based on the result of a medical professional's monitoring of the user. According to another embodiment, the predetermined period may mean a period during which a medical professional adjusts treatment intensity for a user. When a user receives a remote treatment service for the first time, the user may not be familiar with the treatment service. In this case, the user may not easily adapt to the treatment image 142 and may exhibit abnormal behavior. Therefore, it may be important for the medical professional to adjust the intensity of the treatment image 142 while monitoring the user in an initial treatment stage. The predetermined period may be, for example, two weeks. Therefore, during the first two weeks of the treatment, the medical professional may monitor the user and adjust the intensity of the treatment image 142. When the predetermined period according to another embodiment has passed, the server 110 or the user terminal 130 may determine the adjustment of treatment intensity according to the medical professional's a determination.

For a user who passes a predetermined criterion according to another embodiment, the server 110 may adjust the intensity of the treatment image 142 based on treatment pattern information, the biometric information 160, and the feedback information 170 of the user. The user who passes the predetermined criterion according to another embodiment may mean a person whose mental illness is not severe. For example, the user who passes a predetermined criterion may include those with improved symptoms of a mental illness or those with mild symptoms. A medical professional doesn't have to monitor those with mild symptoms to adjust treatment intensity. Also, there may be some patients who do not have a doctor's prescription among those with mild symptoms. For example, some patients do not have a doctor's prescription due to mild symptoms. In order to allow those with mild symptoms to receive a treatment service, the server 110 may adjust the intensity of the treatment image 142, based on treatment pattern information, the biometric information 160, and the feedback information 170 of the user.

The treatment pattern information according to another embodiment may include pattern information generated by using treatment data about a plurality of users of a certain treatment package. For example, the server 110 may extract the pattern information from treatment data of the plurality of users having the same mental illness. The server 110 may extract, from the treatment data, the pattern information about when to increase treatment intensity for patients with a specific phobia and whether to discontinue a treatment. Therefore, the server 110 may adjust the intensity of the treatment image 142 based on the treatment pattern information, the biometric information 160, and the feedback information 170 of the user without a medical professional's diagnosis information.

The server 110 according to another embodiment may transmit a treatment intensity control signal to the user terminal 130 in operation 260. The user terminal 130 may transmit the treatment intensity control signal to the first wearable device 140 in operation 261, based on the treatment intensity control signal. The first wearable device 140 may receive the treatment intensity control signal in operation 261 to adjust the intensity of the treatment image 142 output on a display.

The server 110 according to another embodiment may transmit a treatment end control signal to the user terminal 130 in operation 270. The server 110 may transmit the treatment end control signal when a user receiving treatment reaches a dangerous state. Intensity of the treatment image 142 may refer to intensity that a user may not tolerate. In this case, the user falls into greater fear and a therapeutic effect may be reduced. Accordingly, the server 110 may transmit the treatment end control signal based on the biometric information 160 and/or the feedback information 170. According to another embodiment, the server 110 may determine whether to end a treatment package when the biometric information 160 of the user exceeds a threshold value. For example, the server 110 may discontinue a treatment package when the user's heart rate is 150 or higher. According to another embodiment, based on the feedback information 170, the server 110 may determine whether to end the treatment package. For example, when the user answers to discontinue the treatment in a questionnaire, the server 110 may determine to discontinue the treatment package. The server 110 according to another embodiment may determine to discontinue the treatment package based on first threshold information generated by a medical professional or second threshold information generated based on the treatment pattern information. When the server 110 according to another embodiment determines a threshold value for the biometric information 160, the server 110 may use the first threshold information. That is, the server 110 may determine to discontinue a treatment package using a threshold value determined by a medical professional. For example, when the user's heart rate is 150 or higher and the medical professional determines that a treatment package is to be discontinued, the first threshold information may be 150. According to another embodiment, the second threshold information may be a threshold value generated based on the treatment pattern information. For example, the treatment pattern information may be obtained from treatment data of a plurality of users for the same specific phobia and the server 110 may determine at what level a treatment package may be discontinued through the treatment pattern information. For example, the server 110 may determine to discontinue the treatment package when the user's heart rate is 150 from the treatment pattern information.

According to another embodiment, the user terminal 130 may transmit, to the first wearable device 140, a treatment image end control signal in operation 271. The user terminal 130 may determine to discontinue the treatment package based on the biometric information 160 and/or the feedback information 170. According to another embodiment, the user terminal 130 may receive the treatment end control signal from the server 110 to determine whether to discontinue the treatment package. In this case, the first wearable device 140 may end the treatment image and transmit, to the user terminal 130, a treatment end signal in operation 280. The first wearable device 140 according to another embodiment may receive the treatment end control signal directly from the server 110 to terminate the reproduction of the treatment image 142.

According to another embodiment, the user terminal 130 may store treatment data in a memory in operation 290. The treatment data according to another embodiment may include all data on a series of treatment courses offered to a user. The treatment data may include, for example, information on a mental illness with which the user is diagnosed, a treatment package prescribed to the user, the biometric information 160 of the user, the feedback information 170 of the user, and/or a record on treatment intensity control.

The user terminal 130 according to another embodiment may transmit treatment data to the server 110 in operation 291. The server 110 may receive treatment data in operation 291 and extract the treatment pattern information.

According to another embodiment, a method of operating the server 110 for a remote treatment includes: receiving a treatment request 121 including a user's authentication information; based on the authentication information, transmitting a treatment package corresponding to the treatment request 121 among a plurality of treatment packages 111, 112, 113, and 114 to the user's electronic device, based on the treatment package, outputting the treatment image 142 at a predetermined intensity on a display of an electronic device; receiving at least one of the biometric information 160 of the user and the feedback information 170 of the user to monitor the user's response to the treatment image 142; determining whether to continue the treatment package based on at least one of the biometric information 160 and the feedback information 170; transmitting, to the electronic device, a treatment intensity control signal in operation 270, based on at least one of the biometric information 160 and the feedback information 170 once it is determined to continue the treatment package; and transmitting a treatment image end control signal to the electronic device once it is determined to discontinue the treatment package.

The treatment package according to another embodiment may include at least one of a specific phobia treatment package, a panic disorder treatment package, a social phobia treatment package, a posttraumatic stress disorder (PTSD)

treatment package, an anxiety disorder treatment package, and an obsessive-compulsive disorder (OCD) treatment package.

The treatment request 121 according to another embodiment may include at least one of information about a mental illness with which the user of the treatment request 121 is diagnosed by a medical professional and information about a treatment package which corresponds to a mental illness and is prescribed by a medical professional.

The electronic device according to another embodiment may include at least one wearable device mounted on a part of the user's body and the user terminal 130 for transmitting and receiving data to and from the wearable device.

The wearable device according to another embodiment may include at least one of the first wearable device 140 positioned on the user's head and the second wearable device 150 positioned on a body part other than the user's head.

Outputting the treatment image according to another embodiment may include outputting the treatment image determined based on at least one piece of the following information about: an object determined based on treatment intensity and inducing a mental illness, a period during which a mental illness lasts, a place which induces a mental illness, and a sound which induces a mental illness.

The object information inducing a mental illness according to another embodiment may include at least one of a number of objects, size of the object, a resolution of the object, a density of the object, and distance to the object.

The biometric information 160 of a user according to another embodiment may include at least one of a heart rate, an electrocardiogram, an RR, a blood pressure, a body temperature, a blood oxygen saturation, and a lactate level.

Adjusting the intensity of the treatment image 142 according to another embodiment may include controlling the intensity of the treatment image 142 based on diagnosis information generated by a medical professional based on the biometric information 160 and the feedback information 170 for a predetermined period.

Adjusting the intensity of the treatment image 142 according to another embodiment may include adjusting the intensity of the treatment image 142 for a user who passes a predetermined criterion, based on the treatment pattern information, the biometric information 160, and the user's feedback information 170.

The treatment pattern information according to another embodiment may include pattern information generated by using treatment data about a plurality of users of a certain treatment package.

Adjusting the intensity of the treatment image according to another embodiment may include adjusting the intensity of the treatment image 142 by applying a higher weight to the feedback information 170 than the biometric information 160.

Adjusting the intensity of the treatment image 142 according to another embodiment may include generating prior sign information through an amount of change in first biometric information 410 and second biometric information 430, wherein the first biometric information 410 is biometric information before a treatment event occurs and the second biometric information 430 is biometric information after the treatment event occurs, and adjusting intensity of the treatment image 142 based on the prior sign information.

Determining to discontinue the treatment package according to another embodiment may include determining to discontinue the treatment package based on the prior sign information.

Determining to discontinue the treatment package according to another embodiment includes determining to discontinue the treatment package based on first threshold information generated by a medical professional or second threshold information generated based on the treatment pattern information.

According to another embodiment, determining to discontinue the treatment package may further include transmitting, to an electronic device, a control signal for executing a biofeedback package.

The biofeedback package according to another embodiment may include a package which outputs the biometric information 160 on a display of the electronic device to allow a user to check their biometric information 160 on the display so that the user may control their respiration.

Figure 3:
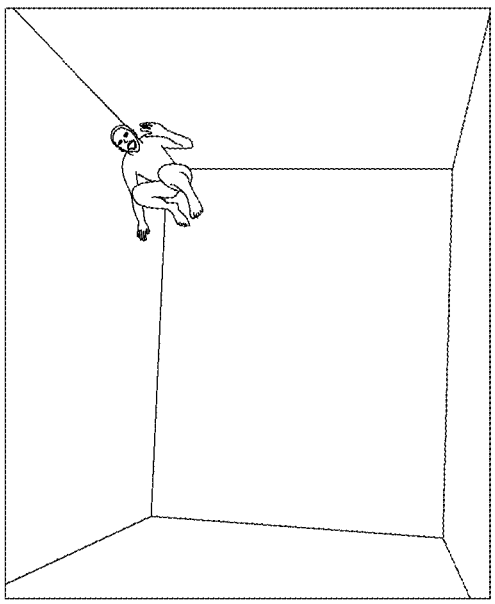
FIG. 3 is a diagram illustrating a treatment package according to an embodiment of the disclosure.

FIG. 3 is a diagram illustrating a treatment package according to an embodiment of the disclosure.

FIG. 3 shows a phobia-type table 300, acrophobia 310, entomophobia 320, and claustrophobia 330.

Referring to FIG. 3, according to one embodiment, a treatment package may include treatment packages for all mental illnesses to which a treatment based on systemic exposure may be applied. The treatment package may include treatment information corresponding to each mental illness. Progressive exposure may be, for example, systematic desensitization.

According to a second embodiment, the systematic desensitization may refer to a behavior modification technique by exposing a patient to anxiety gradually in stages to alleviate or remove the patient's anxiety response. The systematic desensitization may include multiple stages. For example, the first stage may be muscle relaxation training to release tension in the body. The second stage may make an anxiety hierarchical list of 10 to 20 stimuli from a low to a high level. The third stage may be the desensitization stage according to the anxiety hierarchical list, in which an anxiety response is gradually alleviated or eliminated by imagining an anxiety-provoking situation in stages.

According to another embodiment, the treatment package may include at least one of a specific phobia treatment package, a panic disorder treatment package, a social phobia treatment package, a PTSD treatment package, an anxiety disorder treatment package, and an OCD treatment package. The phobia-type table 300 in FIG. 3 may be information included in the specific phobia treatment package. A specific phobia may vary depending on the natural environment, the type of animal, or the type of situation, as shown in FIG. 3. The specific phobia treatment package may store information by phobia in a table. For example, the specific phobia treatment package may include treatment packages for the acrophobia 310, the entomophobia 320, and/or the claustrophobia 330. Also, the specific phobia treatment package may include a treatment image corresponding to each phobia type, according to intensity. The treatment package described herein is merely an example, and the disclosure is not limited thereto.

A method of providing a treatment service, according to another embodiment, may include a method of controlling a user's senses to psychologically overcome the user's specific phobia. The user may acquire most information from sight. Providing visual information for the user may be largely categorized into changing a scene or a background and indicating a target or an object on a display. In this case, a server 110 and/or a user terminal 130 may control a scene or an object based on medical grounds. Immersiveness may be critical to the scene or the object according to another embodiment. In particular, it may be appropriate to display the scene in virtual reality (VR) rather than in augmented reality (AR). For example, an airplane or an elevator may be displayed with graphics to give a feeling of immersiveness to surrounding environments and treatment intensity corresponding to a phobia may be estimated based on period, resolution, and other variables. An object according to another embodiment may display a specific object (e.g., an insect) and check a user's reaction by controlling the movement, size, and activity level of the object as variables. AR may be more effective than VR to display the object. Accordingly, such a phobia-related treatment package may include not only image information of the object displayed on a display, but also information about deformation of the object depending on treatment intensity.

A method of treating a mental illness (e.g., a specific phobia), according to another embodiment, may be training a user to gradually overcome the trauma from a certain fear. It may be necessary to identify a category for correct treatment for a mental illness (e.g., treatment for a specific phobia) and to provide a treatment package tailored to a user's situation.

According to another embodiment, the server 110 having treatment packages for various types of mental illnesses and providing a treatment package corresponding to a treatment request 121 may allow patients to be treated for various types of mental illnesses without visiting a medical institution.

FIG. 4 is a diagram illustrating prior signs according to an embodiment of the disclosure.

FIG. 4 illustrates biometric information by session 400, second session biometric information 401, first biometric information 410, second biometric information 430, a treatment event 420, a heart rate 471, blood pressure 472, a stress index 473, treatment image intensity 474, a second session 450, and a fifth session 460.

A server 110 according to one embodiment may receive biometric information 160 from a second wearable device 150.

Referring to FIG. 4, the biometric information 160 may be displayed according to session or time (e.g., 1 minute intervals) in a specific session.

The server 110 according to a second embodiment may adjust the treatment image intensity 474. The server 110 according to another embodiment may adjust the treatment image intensity 474 based on the biometric information 160 and/or feedback information 170. A user terminal 130 according to another embodiment may adjust the treatment image intensity 474.

The server 110 according to another embodiment may generate prior sign information through an amount of change in the first biometric information 410 and the second biometric information 430, wherein the first biometric information 410 is biometric information before the treatment event 420 and the second biometric information 430 is biometric information after the treatment event 420. The prior sign information according to another embodiment may include information on a sign that appears before a specific mental illness is manifested in a user. The server 110 may generate the prior sign information based on an amount of change between the first biometric information 410 and the second biometric information 430 and adjust the treatment image intensity 474 using the prior sign information. For example, the blood pressure 472 of a user in the first biometric information 410 may be 120/80. When the treatment event 420 of outputting a treatment image 142 to the user on a display starts, the blood pressure 472 of the user may rapidly rise to 150/90. It may be seen that the blood pressure 472 of the user gradually decreases in the second biometric information 430 after the treatment event 420.

The server 110 according to another embodiment may adjust the treatment image intensity 474 based on the prior sign information. The server 110 according to another embodiment may lower the treatment image intensity 474 or discontinue a treatment package when an amount of change is substantial between the first biometric information 410 and the second biometric information 430, which are biometric information before and after the treatment event 420. The server 110 according to another embodiment may increase the treatment image intensity 474 when an amount of change is small between the first biometric information 410 and the second biometric information 430, which are biometric information before and after the treatment event 420.

The server 110 according to another embodiment may determine to discontinue a treatment package. The server 110 may determine to discontinue the treatment package, based on the prior sign information. When a user is highly likely to develop a mental illness based on the prior sign information, the server 110 may determine to discontinue the treatment package. For example, the heart rate 471, the blood pressure 472, and/or the stress index 473 may abruptly increase in the second session 450 in the biometric information by session 400. Because the treatment image intensity 474 in the second session 450 is 9, which increases by three stages compared to the previous session. When the treatment image intensity 474 increases and the biometric information 160 of the user in the second session 450 exceeds a threshold value, the server 110 may determine to discontinue the treatment package.

The server 110 according to another embodiment may adjust the treatment image intensity 474 based on the biometric information by session 400. For example, the server 110 may increase the treatment image intensity 474 to 6 in the fifth session 460 in the biometric information by session 400. In this case, the heart rate 471, the blood pressure 472, and the stress index 473 of the user may slightly increase. When it is determined that the treatment image intensity 474 is unbearable to the user based on the increased biometric information 160 of the user, the server 110 may lower the treatment image intensity 474 to 2 in 6th and 7th sessions. For example, the server 110 may increase the treatment image intensity 474 to 6 in the fifth session 460, in the biometric information 160 by session 400. In 3rd and 4th sessions, the heart rate 471, the blood pressure 472, and the stress index 473 of the user may be in normal ranges. When it is determined that the user may endure the treatment image intensity 474 based on the biometric information 160 of the user, the server 110 may increase the treatment image intensity 474 to 6 in the fifth session 460 to increase a treatment effect.

The intensity of treatment according to another embodiment may have a preset stage by treatment package. The server 110 according to another embodiment may adjust the intensity of treatment by controlling information about an object inducing fear (e.g., number, size, activity, immersiveness, and/or resolution). The intensity of treatment according to another embodiment may be determined by at least one piece of the following information: an object triggering mental illness depending on the intensity of treatment, a period of a situation triggering the mental illness, a place triggering the mental illness, and a sound triggering the mental illness.

FIG. 5 is a diagram illustrating the adjustment of treatment intensity according to an embodiment of the disclosure.

FIG. 5 shows biometric information on a display 500, May 3rd treatment data 510, May 4th treatment data 520, May 7th treatment data 530, a date 541, treatment image intensity 542, tolerability 543, a symptom 544, a heart rate 545, blood pressure 546, and a stress index 547.

Referring to FIG. 5, a server 110 according to one embodiment may adjust the treatment image intensity 542 based on biometric information 160 included in treatment data according to date. For example, the treatment image intensity 542 included in the May 3rd treatment data 510 may be 2. When the treatment image intensity 542 is 2, a user may not be greatly bewildered or stressed out. Therefore, the server 110 may increase the treatment image intensity 542 to 3 on the next day. The treatment image intensity 542 included in the May 4th treatment data 520 may be 3. Since the treatment image intensity 542 increases, the heart rate 545 of the user may rise to 110. However, since the stress index 547 of the user shows a middle level (Mid), the server 110 may determine to continue a treatment package.

The server 110 according to a second embodiment may determine to discontinue a treatment package based on the biometric information 160. For example, the treatment image intensity 542 included in the May 7th treatment data 530 may be 4. In this case, since the user may not withstand the treatment image intensity 542, the tolerability 543 may be displayed as X. The tolerability 543 may refer to a degree to which a patient or a clinical subject may tolerate side effects or discomfort when treatment initiates. Therefore, the server 110 may discontinue a treatment package and skip treatment on the next day, May 8.

The server 110 according to another embodiment may determine to discontinue a treatment package based on feedback information 170. The feedback information 170 may, for example, include a user's answer obtained through a survey. For example, a question may be "Are you sure you want to discontinue this treatment package?". To respond to this question, when the user feels a lot of fear, they may answer "yes". The server 110 may discontinue the treatment package based on the feedback information 170 of the user. According to another embodiment, when the user has tolerability to the treatment image intensity 542, the answer may be "no". In this case, the server 110 may continue the treatment package based on the feedback information 170 of the user.

The server 110 according to another embodiment may adjust the treatment image intensity 542. The server 110 may adjust the treatment image intensity 542 by applying a higher weight to the feedback information 170 of the user than the biometric information 160. For example, based on the biometric information 160 included in the May 4th treatment data 520, the user's tolerability to 3 for the treatment image intensity 542, may be "0". That is, it may be analyzed that the user may withstand 3 for the treatment image intensity 542, based on the biometric information 160. However, according to the user's subjective judgment, the user may feel difficult to withstand 3 for the treatment image intensity 542. In this case, the user may transmit the feedback information 170 to the server 110. For example, the feedback information 170 may include information, such as "I want to stop treatment because I cannot withstand 3 for the treatment image intensity 542". In this case, the server 110 may stop the treatment package and determine to skip treatment on the next day, May 5. The server 110 may consider both objective information on how the user responds to the treatment image intensity 542 and subjective information to determine the treatment image intensity 542. However, the objective information, such as the biometric information 160, may be insufficient to determine the user's tolerability. Accordingly, the server 110 may determine whether the user may continue treatment by applying a higher weight to the feedback information 170, which is the user's subjective information.

Figure 6:
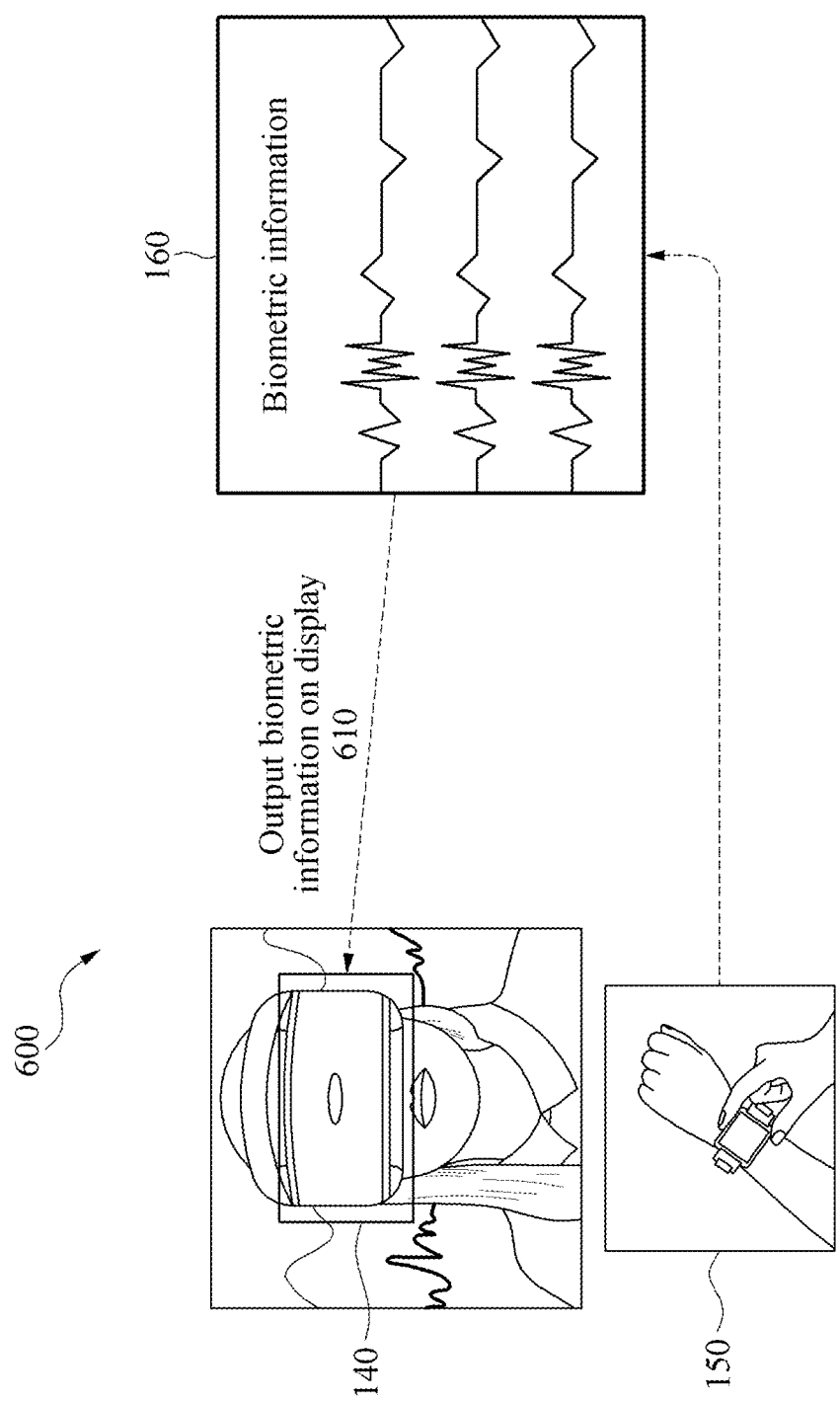
FIG. 6 is a diagram illustrating biofeedback according to an embodiment of the disclosure.

FIG. 6 is a diagram illustrating biofeedback according to an embodiment of the disclosure.

FIG. 6 shows a biofeedback diagram using a wearable device 600, a first wearable device 140, a second wearable device 150, and biometric information 160.

Referring to FIG. 6, a server 110 according to another embodiment may provide biofeedback to a user. A user terminal 130 according to another embodiment may provide the biofeedback to the user. When a user views a treatment image at the intensity that the user may not tolerate, the user's heart rate and respiration rate may rise rapidly and fall into a dangerous state. In this case, the server 110 may provide the biofeedback to the user using an electronic device to stabilize the user's heart rate and respiration rate.

The biofeedback according to another embodiment may include a method of quantifying physiological information, such as a patient's respiration rate and heart rate, so that the patient may see the information with their eyes to self-regulate the response of an autonomic nervous system, which may not be consciously known or controlled in a normal state. The biofeedback may refer to providing a patient with visual or audio data of specific findings on physiological differences in tension and relaxation so as to allow the patient to control symptom-related physiological variables through self-training.

The server 110 according to another embodiment may transmit a control signal for executing a biofeedback package to an electronic device. The biofeedback package according to another embodiment may include a package which outputs the biometric information 160 on a display of an electronic device to allow a user to check their biometric information 160 on the display so that the user may control their respiration.

The server 110 according to another embodiment may receive the biometric information 160 and/or feedback information 170 from the second wearable device 150. The server 110 may determine whether to transmit a control signal for executing the biofeedback package to the user terminal 130, based on the biometric information 160 and/or the feedback information 170. For example, when a user's tolerability is "X" or the user's heart rate or respiration rate is equal to or greater than a predetermined standard, the server 110 may transmit a control signal for executing the biofeedback package to the user terminal 130.

When the user terminal 130 according to another embodiment receives the control signal for executing the biofeedback package, the biometric information 160 of the user may be output on a display of the second wearable device 150 in operation 610. The biometric information 160 of the user according to one embodiment may also be output on a display of the user terminal 130.

Figure 7:
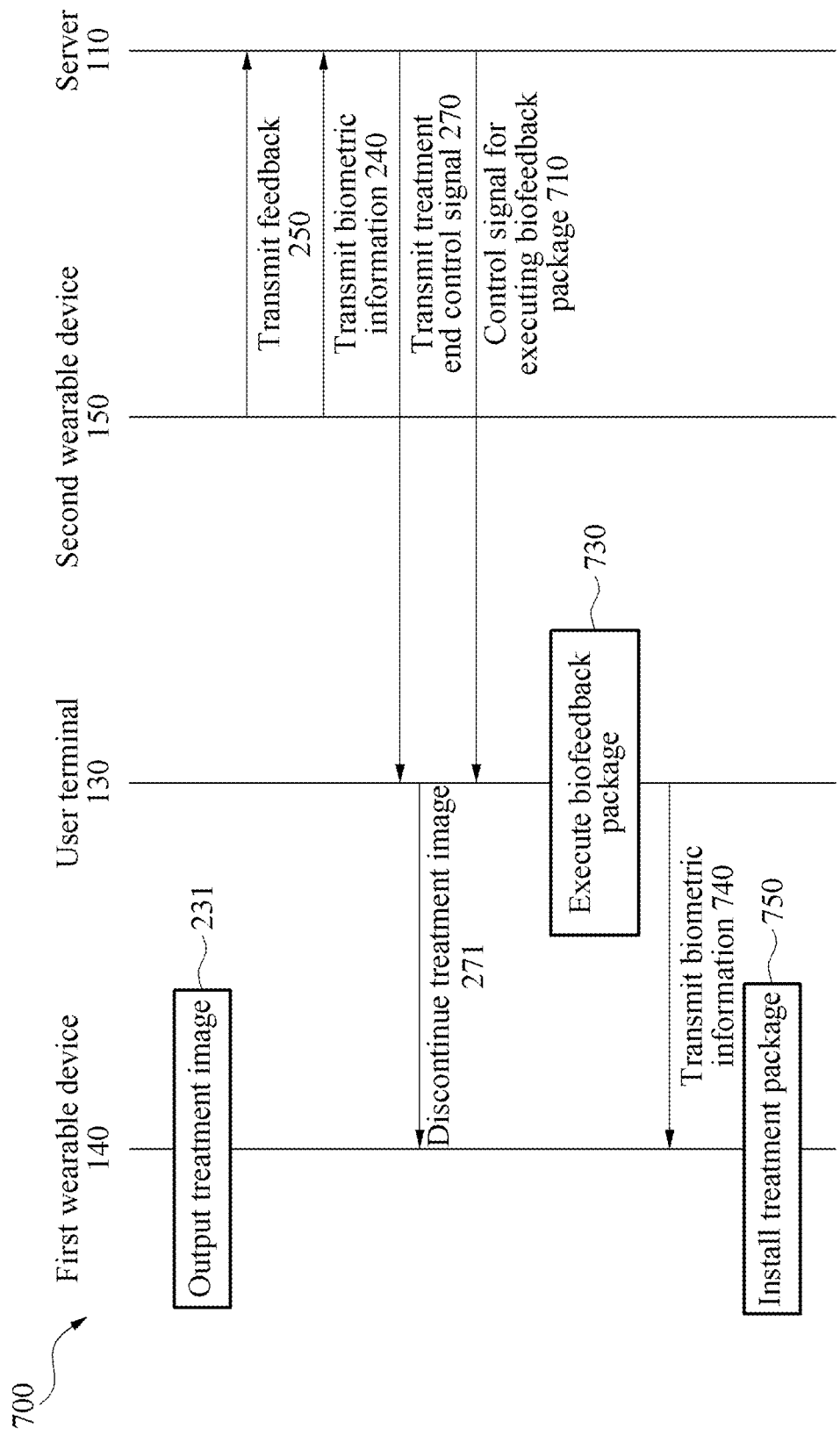
FIG. 7 is a flowchart illustrating a method of providing biofeedback to a user, according to an embodiment of the disclosure.

FIG. 7 is a flowchart illustrating a method of providing biofeedback to a user, according to an embodiment of the disclosure.

Referring to FIG. 7, a first wearable device 140 according to one embodiment may output a treatment image via a display in operation 231. An electronic device that displays a treatment image may be a second wearable device 150 or a user terminal 130 but is not limited to the first wearable device 140.

In a method 700, a server 110 according to a second embodiment may receive feedback information 170 from the second wearable device 150 in operation 250 or receive biometric information 160 from the second wearable device 150 in operation 240. As the server 110 does, the user terminal 130 according to another embodiment may receive the feedback information 170 from the second wearable device 150 in operation 251 or receive the biometric information 160 from the second wearable device 150 in operation 241.

The server 110 according to another embodiment may transmit a treatment end control signal to the user terminal 130 in operation 270. The user terminal 130 may transmit the treatment end control signal to the first wearable device 140 in operation 271 upon receipt of the treatment end control signal from the server 110 or under the a determination of the user terminal 130.

Upon transmission of the treatment end control signal, the server 110 according to another embodiment may transmit a signal of controlling the execution of a biofeedback package to the user terminal 130 in operation 710. In this case, the user terminal 130 may execute the biofeedback package in operation 730. The first wearable device 140 may receive the biometric information 160 from the user terminal 130, the second wearable device 150, or the server 110 in operation 740. The first wearable device 140 may output the received biometric information 160 on a display in operation 750. A user's current respiration rate, heart rate, and oxygen saturation may be displayed on a display of the first wearable device 140. The user may stabilize breathing while viewing their biometric information 160 on the display. A respiration guidance image for stabilizing a user's respiration may be output on a display of the first wearable device 140 according to another embodiment.

Figure 8A:
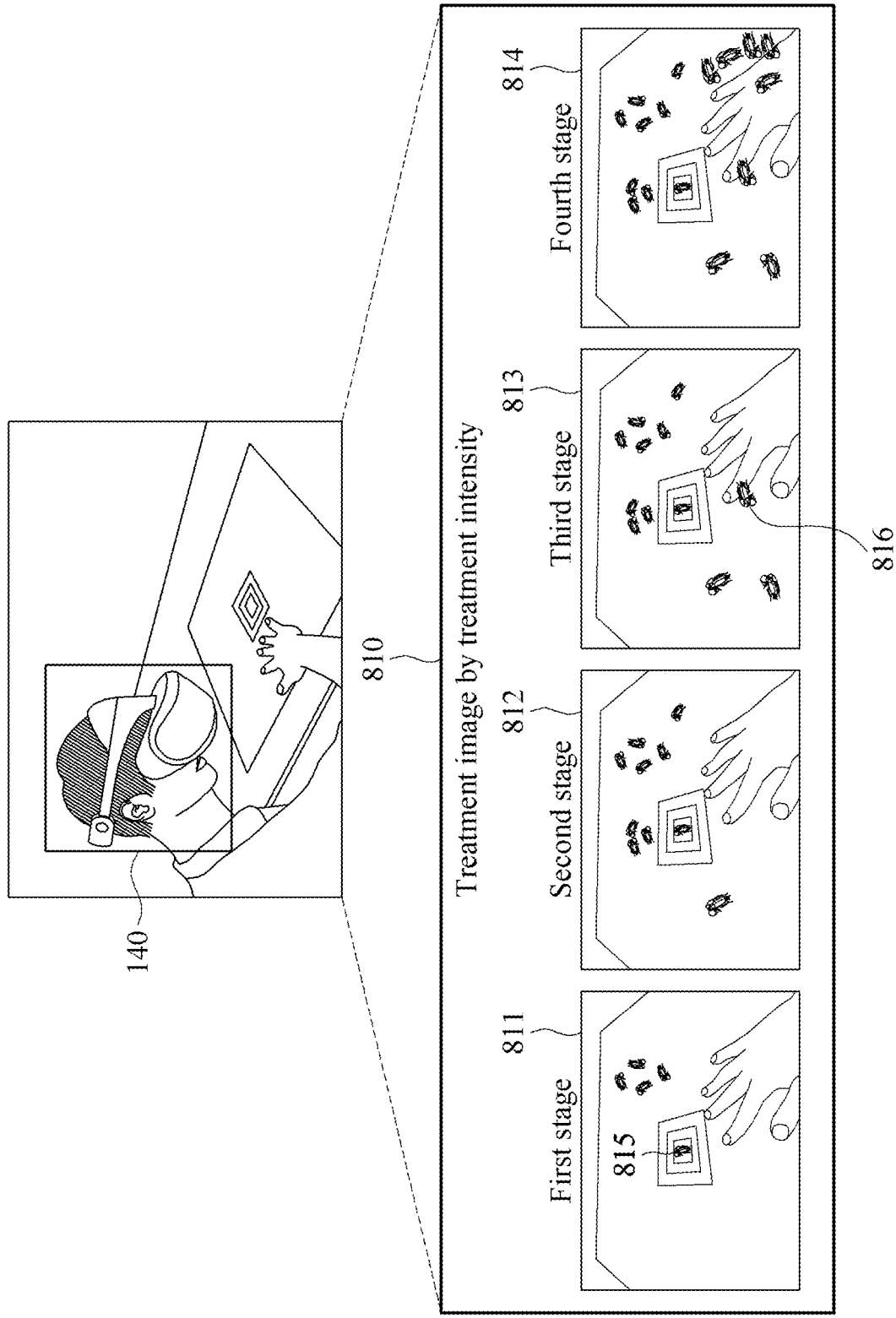
FIGS. 8A, 8B, and 8C are diagrams illustrating treatment intensity according to various embodiments of the disclosure.
Figure 8B:
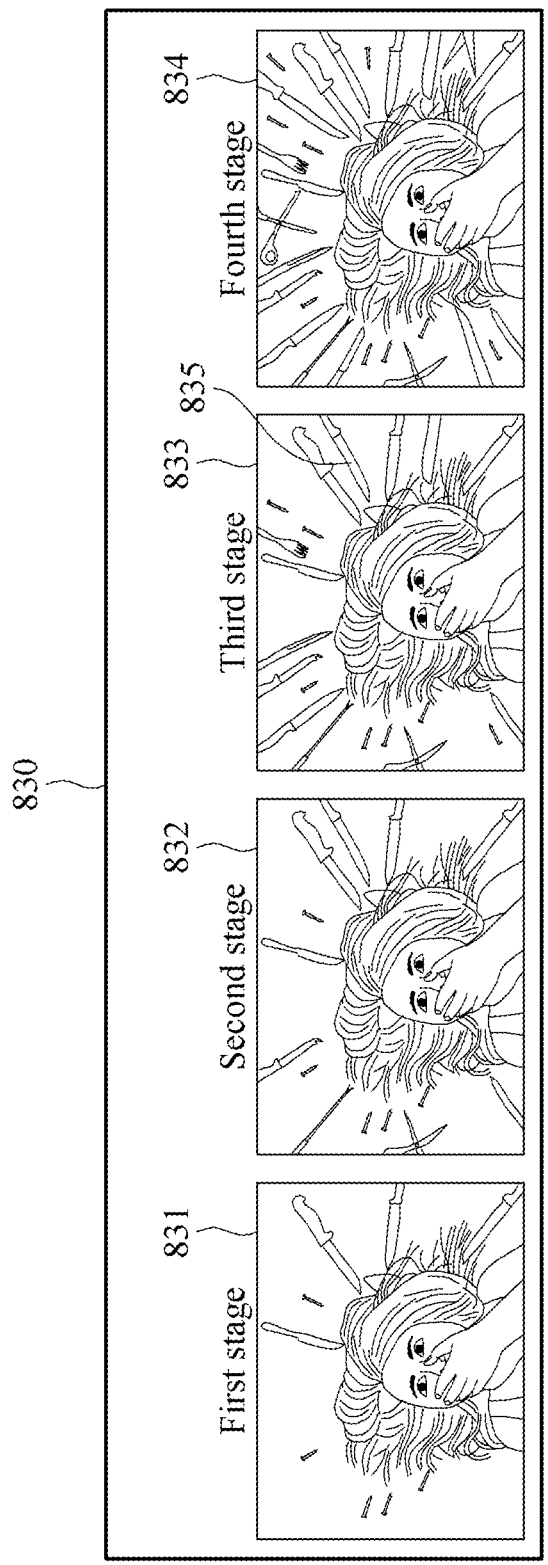
Figure 8C:
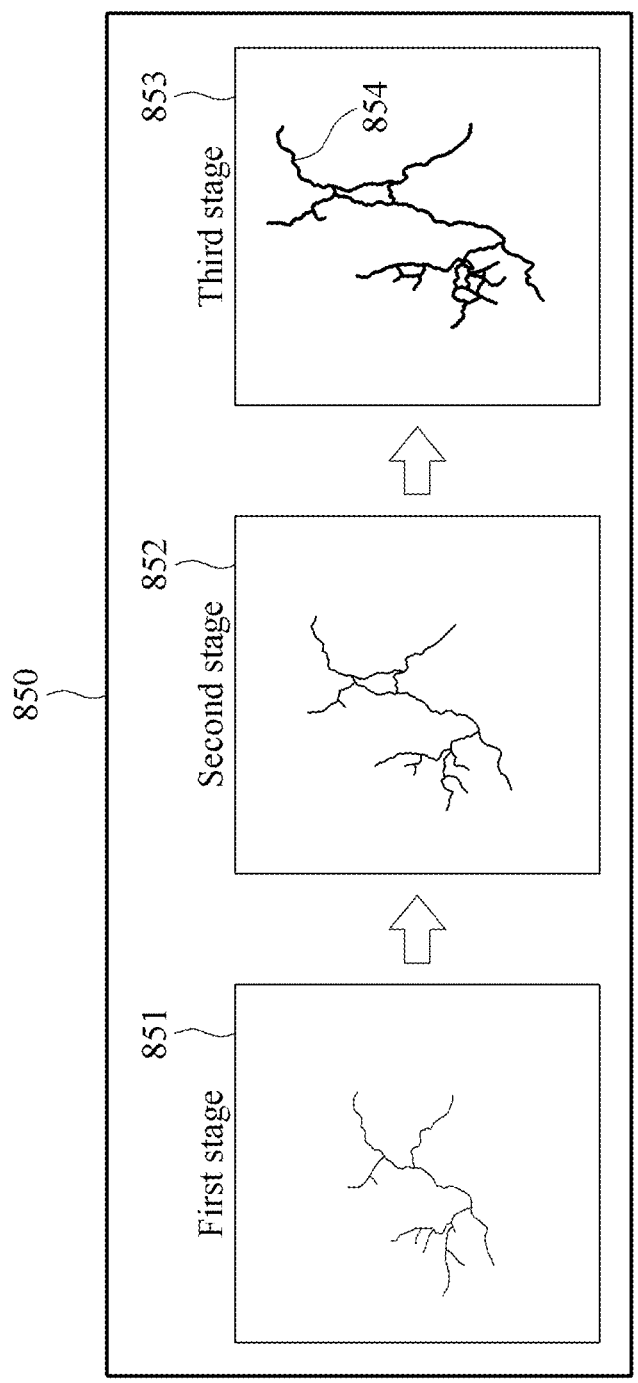

FIGS. 8A, 8B, and 8C are drawings illustrating treatment intensity according to various embodiments of the disclosure.

FIG. 8A shows a user wearing a first wearable device 140 on their head. Treatment images 810 according to intensity on a display of the first wearable device 140 are also shown in FIG. 8A. Additionally, first objects 815 and second objects 816, which induce fear, are shown.

A treatment image according to one embodiment may be determined based on treatment intensity. The treatment image according to a second embodiment may include a treatment image determined by at least one piece of the following information: an object triggering mental illness, a period of a situation triggering the mental illness, a place triggering the mental illness, and a sound triggering the mental illness. The object triggering the mental illness may be, for example, a cockroach, a knife, a spider, or a snake. The duration of a situation triggering the mental illness may include, for example, a period during which a claustrophobic person is confined in a closed room. The place triggering a mental illness may be, for example, an airplane, an elevator, or a plaza. The sound triggering the mental illness may be, for example, the sound of thunder and lightning. The foregoing is merely an example, and the disclosure is not limited thereto.

The object information inducing a mental illness according to another embodiment may include at least one of a number of objects, size of the object, resolution of the object, density of the object, and distance to the object.

Referring to FIG. 8A, the object triggering a mental illness may be, for example, a first object 815, represented by a cockroach. A server 110 according to another embodiment may increase the number (or the size, or the amount of activity) of objects as treatment intensity increases. For example, the number of first objects 815 may be 5 for treatment intensity 1 of stage 811. As the treatment intensity increases to a second stage 812, to a third stage 813, and to a fourth stage 814, the number (or the size or the amount of activity) of first objects 815 triggering a mental illness may gradually increase.

The server 110 according to another embodiment may shorten a distance between a user and an object as the treatment intensity increases. As shown in the third stage 813 of FIG. 8A, the second object 816 is on the user's finger. However, in a first stage 811, the first object 815 is separated from the user's hand by a predetermined distance. The closer the user is from the object, the greater fear the user may have. Therefore, the server 110 may adjust treatment intensity by controlling a distance between the user and the object.

FIG. 8B illustrates that the greater the treatment intensity, the greater a number of objects triggering mental illness.

Referring to FIG. 8B, an object triggering mental illness may be a sharp object, that is, a third object 835.

As the intensity of a treatment image increases from a first stage 831, to a second stage 832, to a third stage 833, and to a fourth stage 834, the server 110 according to another embodiment may increase the number of third objects 835 and decrease a distance between the third object 835 and the user.

FIG. 8C illustrates that the greater the treatment intensity, the higher the resolution of an object triggering a mental disorder.

Referring to FIG. 8C, as the intensity of a treatment image increases from a first stage 851, to a second stage 852, and to a third stage 853, a fourth object 854 triggering a mental illness may have higher resolution.

FIG. 9 is a block diagram illustrating an electronic device in a network environment according to an embodiment of the disclosure.

Referring to FIG. 9, an electronic device 1001 in a network environment 1000 may communicate with an electronic device 1002 via a first network 1098 (e.g., a short-range wireless communication network), or communicate with at least one of an electronic device 1004 or a server 1008 via a second network 1099 (e.g., a long-range wireless communication network). According to one embodiment, the electronic device 1001 may communicate with the electronic device 1004 via the server 1008. According to a second embodiment, the electronic device 1001 may include a processor 1020, a memory 1030, an input module 1050, a sound output module 1055, a display module 1060, an audio module 1070, and a sensor module 1076, an interface 1077, a connecting terminal 1078, a haptic module 1079, a camera module 1080, a power management module 1088, a battery 1089, a communication module 1090, a subscriber identification module (SIM) 1096, or an antenna module 1097. In some example embodiments, at least one (e.g., the connecting terminal 1078) of the above components may be omitted from the electronic device 1001, or one or more other components may be added in the electronic device 1001. In some example embodiments, some (e.g., the sensor module 1076, the camera module 1080, or the antenna module 1097)

of the components may be integrated as a single component (e.g., the display module 1060).

The processor 1020 may execute, for example, software (e.g., a program 1040) to control at least one other component (e.g., a hardware or software component) of the electronic device 1001 connected to the processor 1020, and may perform various data processing or computation. According to another embodiment, as at least a part of data processing or computation, the processor 1020 may store a command or data received from another component (e.g., the sensor module 1076 or the communication module 1090) in a volatile memory 1032, process the command or the data stored in the volatile memory 1032, and store resulting data in a non-volatile memory 1034. According to another embodiment, the processor 1020 may include a main processor 1021 (e.g., a central processing unit (CPU) or an application processor) or an auxiliary processor 1023 (e.g., a graphics processing unit (GPU), a neural processing unit (NPU), an image signal processor (ISP), a sensor hub processor, or a communication processor (CP)) that is operable independently of, or in conjunction with the main processor 1021. For example, when the electronic device 1001 includes the main processor 1021 and the auxiliary processor 1023, the auxiliary processor 1023 may be adapted to consume less power than the main processor 1021 or to be specific to a specified function. The auxiliary processor 1023 may be implemented separately from the main processor 1021 or as a part of the main processor 1021.

The auxiliary processor 1023 may control at least some of functions or states related to at least one (e.g., the display module 1060, the sensor module 1076, or the communication module 1090) of the components of the electronic device 1001, instead of the main processor 1021 while the main processor 1021 is in an inactive (e.g., sleep) state or along with the main processor 1021 while the main processor 1021 is an active state (e.g., executing an application). According to another embodiment, the auxiliary processor 1023 (e.g., an ISP or a CP) may be implemented as a portion of another component (e.g., the camera module 1080 or the communication module 1090) that is functionally related to the auxiliary processor 1023. According to another embodiment, the auxiliary processor 1023 (e.g., an NPU) may include a hardware structure specified for artificial intelligence model processing. An artificial intelligence model may be generated by machine learning. Such learning may be performed by, for example, the electronic device 1001 in which artificial intelligence is performed, or may be performed via a separate server (e.g., the server 1008). Learning algorithms may include, but are not limited to, for example, supervised learning, unsupervised learning, semi-supervised learning, or reinforcement learning. The AI model may include a plurality of artificial neural network layers. An artificial neural network may include, for example, a deep neural network (DNN), a convolutional neural network (CNN), a recurrent neural network (RNN), a restricted Boltzmann machine (RBM), a deep belief network (DBN), and a bidirectional recurrent deep neural network (BRDNN), a deep Q-network, or a combination of two or more thereof, but is not limited thereto. The artificial intelligence model may additionally or alternatively, include a software structure other than the hardware structure.

The memory 1030 may store various data used by at least one component (e.g., the processor 1020 or the sensor module 1076) of the electronic device 1001. The various data may include, for example, software (e.g., the program 1040) and input data or output data for a command related thereto. The memory 1030 may include the volatile memory 1032 or the non-volatile memory 1034.

The program 1040 may be stored as software in the memory 1030, and may include, for example, an operating system (OS) 1042, middleware 1044, or an application 1046.

The input module 1050 may receive a command or data to be used by another component (e.g., the processor 1020) of the electronic device 1001, from the outside (e.g., a user) of the electronic device 1001. The input module 1050 may include, for example, a microphone, a mouse, a keyboard, a key (e.g., a button), or a digital pen (e.g., a stylus pen).

The sound output module 1055 may output a sound signal to the outside of the electronic device 1001. The sound output module 1055 may include, for example, a speaker or a receiver. The speaker may be used for general purposes, such as playing multimedia or playing record. The receiver may be used to receive an incoming call. According to another embodiment, the receiver may be implemented separately from the speaker or as a part of the speaker.

The display module 1060 may visually provide information to the outside (e.g., a user) of the electronic device 1001 (e.g., a user). The display module 1060 may include, for example, a control circuit for controlling a display, a hologram device, or a projector and control circuitry to control a corresponding one of the display, the hologram device, and the projector. According to another embodiment, the display module 1060 may include a touch sensor adapted to sense a touch, or a pressure sensor adapted to measure an intensity of a force incurred by the touch.

The audio module 1070 may convert a sound into an electric signal or vice versa. According to another embodiment, the audio module 1070 may obtain the sound via the input module 1050 or output the sound via the sound output module 1055 or an external electronic device (e.g., the electronic device 1002 such as a speaker or a headphone) directly or wirelessly connected to the electronic device 1001.

The sensor module 1076 may detect an operational state (e.g., power or temperature) of the electronic device 1001 or an environmental state (e.g., a state of a user) external to the electronic device 1001, and generate an electric signal or data value corresponding to the detected state. According to another embodiment, the sensor module 1076 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1077 may support one or more specified protocols to be used for the electronic device 1001 to be coupled with the external electronic device (e.g., the electronic device 1002) directly (e.g., wiredly) or wirelessly. According to another embodiment, the interface 1077 may include, for example, a high-definition multimedia interface (HDMI), a universal serial bus (USB) interface, a secure digital (SD) card interface, or an audio interface.

The connecting terminal 1078 may include a connector via which the electronic device 1001 may be physically connected to an external electronic device (e.g., the electronic device 1002). According to another embodiment, the connecting terminal 1078 may include, for example, an HDMI connector, a USB connector, an SD card connector, or an audio connector (e.g., a headphone connector).

The haptic module 1079 may convert an electric signal into a mechanical stimulus (e.g., a vibration or a movement) or an electrical stimulus which may be recognized by a user via his or her tactile sensation or kinesthetic sensation. According to another embodiment, the haptic module 1079 may include, for example, a motor, a piezoelectric element, or an electric stimulator.

The camera module 1080 may capture still images and moving images. According to another embodiment, the camera module 1080 may include one or more lenses, image sensors, image signal processors, or flashes.

The power management module 1088 may manage power supplied to the electronic device 1001. According to another embodiment, the power management module 1088 may be implemented as, for example, at least a part of a power management integrated circuit (PMIC).

The battery 1089 may supply power to at least one component of the electronic device 1001. According to another embodiment, the battery 1089 may include, for example, a primary cell which is not rechargeable, a secondary cell which is rechargeable, or a fuel cell.

The communication module 1090 may support establishing a direct (e.g., wired) communication channel or a wireless communication channel between the electronic device 1001 and the external electronic device (e.g., the electronic device 1002, the electronic device 1004, or the server 1008) and performing communication via the established communication channel. The communication module 1090 may include one or more communication processors that are operable independently of the processor 1020 (e.g., an application processor) and that support a direct (e.g., wired) communication or a wireless communication. According to another embodiment, the communication module 1090 may include a wireless communication module 1092 (e.g., a cellular communication module, a short-range wireless communication module, or a global navigation satellite system (GNSS) communication module) or a wired communication module 1094 (e.g., a local area network (LAN) communication module, or a power line communication (PLC) module). A corresponding one of these communication modules may communicate with the external electronic device 1004 via the first network 1098 (e.g., a short-range communication network, such as Bluetooth™, wireless-fidelity (Wi-Fi) direct, or infrared data association (IrDA)) or the second network 1099 (e.g., a long-range communication network, such as a legacy cellular network, a 5$^{th}$ generation (5G) network, a next-generation communication network, the Internet, or a computer network (e.g., a LAN or a wide area network (WAN)). These various types of communication modules may be implemented as a single component (e.g., a single chip), or may be implemented as multi components (e.g., multi chips) separate from each other. The wireless communication module 1092 may identify and authenticate the electronic device 1001 in a communication network, such as the first network 1098 or the second network 1099, using subscriber information (e.g., international mobile subscriber identity (IMSI)) stored in the SIM 1096.

The wireless communication module 1092 may support a 5G network after a 4th generation (4G) network, and a next-generation communication technology, e.g., a new radio (NR) access technology. The NR access technology may support enhanced mobile broadband (eMBB), massive machine type communications (mMTC), or ultra-reliable and low-latency communications (URLLC). The wireless communication module 1092 may support a high-frequency band (e.g., a millimeter wave (mmWave) band) to achieve, e.g., a high data transmission rate. The wireless communication module 1092 may support various technologies for securing performance on a high-frequency band, such as, e.g., beamforming, massive multiple-input and multiple-output (MIMO), full dimensional MIMO (FD-MIMO), an array antenna, analog beam-forming, or a large scale antenna. The wireless communication module 1092 may support various requirements specified in the electronic device 1001, an external electronic device (e.g., the electronic device 1004), or a network system (e.g., the second network 1099). According to another embodiment, the wireless communication module 1092 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 1097 may transmit or receive a signal or power to or from the outside (e.g., the external electronic device) of the electronic device 1001. According to another embodiment, the antenna module 1097 may include an antenna including a radiating element including a conductive material or a conductive pattern formed in or on a substrate (e.g., a printed circuit board (PCB)). According to another embodiment, the antenna module 1097 may include a plurality of antennas (e.g., array antennas). In such a case, at least one antenna appropriate for a communication scheme used in a communication network, such as the first network 1098 or the second network 1099, may be selected by, for example, the communication module 1090 from the plurality of antennas. The signal or the power may be transmitted or received between the communication module 1090 and the external electronic device via the at least one selected antenna. According to another embodiment, another component (e.g., a radio frequency integrated circuit (RFIC)) other than the radiating element may be additionally formed as a part of the antenna module 1097.

According to various embodiments, the antenna module 1097 may form a mmWave antenna module. According to another embodiment, the mmWave antenna module may include a PCB, an RFIC disposed on a first surface (e.g., a bottom surface) of the PCB or adjacent to the first surface and capable of supporting a designated a high-frequency band (e.g., the mmWave band), and a plurality of antennas (e.g., array antennas) disposed on a second surface (e.g., a top or a side surface) of the PCB, or adjacent to the second surface and capable of transmitting or receiving signals in the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to another embodiment, commands or data may be transmitted or received between the electronic device 1001 and the external electronic device 1004 via the server 1008 coupled with the second network 1099. Each of the external electronic devices 1002 and 1004 may be a device of the same type as or a different type from the electronic device 1001. According to another embodiment, all or some of operations to be executed by the electronic device 1001 may be executed at one or more of the external electronic devices 1002, 1004, and the server 1008. For example, if the electronic device 1001 needs to perform a function or a service automatically, or in response to a request from a user or another device, the electronic device 1001, instead of, or in addition to, executing the function or the service, may request one or more external electronic devices to perform at least part of the function or the service.

The one or more external electronic devices receiving the request may perform the at least part of the function or the service requested, or an additional function or an additional service related to the request, and may transfer an outcome of the performing to the electronic device 1001. The electronic device 1001 may provide the outcome, with or without further processing of the outcome, as at least part of a reply to the request. To that end, a cloud computing, distributed computing, mobile edge computing (MEC), or client-server computing technology may be used, for example. The electronic device 1001 may provide ultra low-latency services using, e.g., distributed computing or mobile edge computing. In another embodiment, the external electronic device 1004 may include an Internet-of-things (IoT) device. The server 1008 may be an intelligent server using machine learning and/or a neural network. According to another embodiment, the external electronic device 1004 or the server 1008 may be included in the second network 1099. The electronic device 1001 may be applied to intelligent services (e.g., smart home, smart city, smart car, or healthcare) based on 5G communication technology or IoT-related technology.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A method of operating a server for remote treatment of a fear based mental illness, the method comprising:
   receiving a treatment request including authentication information of a user and a request for treating the fear based mental illness with which the user is diagnosed;
   transmitting, to an electronic device of the user, a treatment package, including a treatment image, corresponding to the treatment request from among a plurality of treatment packages, based on the authentication information and the fear based mental illness, causing the treatment image to be output at an intensity based on the treatment package via a display of the electronic device;
   receiving at least one of biometric information of the user and feedback information of the user based on a response from the electronic device of the user to the treatment image, wherein the at least one of biometric information includes a first biometric information and a second biometric information;
   receiving a treatment intensity control signal based on the at least one of biometric information and the feedback information;
   determining whether to continue the treatment package based on treatment pattern information, the at least one of biometric information, and the feedback information;
   generating prior sign information based on an amount of change in the first biometric information and the second biometric information;
   adjusting the intensity of the treatment image to be output based on the treatment pattern information, the at least one of biometric information, the feedback information, and the prior sign information;
   transmitting, to the electronic device, a first control signal for adjusting the intensity of the treatment image, according to a determination to continue the treatment package; and
   transmitting, to the electronic device, a second control signal for discontinuing a display of the treatment image, according to a determination to discontinue the treatment package,
   wherein the adjusting of the intensity of the treatment image comprises changing a number of instances of an object within the treatment image based on the treatment pattern information, the at least one of biometric information, and the feedback information, changing a size of the object within the treatment image based on the treatment pattern information, the at least one of biometric information, and the feedback information, changing a resolution of the object within the treatment image based on the treatment pattern information, the at least one of biometric information, and the feedback information, changing a density of the object within the treatment image based on the treatment pattern information, the at least one of biometric information, and the feedback information, changing a proximity of the object within the treatment image based on the treatment pattern information, the at least one of biometric information, and the feedback information, and changing a duration of exposure to the object within the treatment image based on the treatment pattern information, the at least one of biometric information, and the feedback information.

2. The method of claim 1, wherein the treatment package comprises at least one of a specific phobia treatment package, a panic disorder treatment package, a social phobia treatment package, a posttraumatic stress disorder (PTSD) treatment package, an anxiety disorder treatment package, and an obsessive-compulsive disorder (OCD) treatment package.

3. The method of claim 1, wherein the treatment request comprises at least one of information about the fear based mental illness with which the user of the treatment request is diagnosed by a medical professional and information about the treatment package corresponding to the fear based mental illness information prescribed by the medical professional.

4. The method of claim 1, wherein the electronic device comprises at least one wearable device mounted on a part of a body of the user and a user terminal configured to transmit and receive data to and from the at least one wearable device.

5. The method of claim 4, wherein the at least one wearable device comprises a first wearable device positioned on a head of the user and a second wearable device positioned on a user's body part other than the head.

6. The method of claim 1, further comprising outputting the treatment image,
   wherein the outputting of the treatment image is based on at least one of:
      information about an object which induces the fear based mental illness,
      information about a period during which the fear based mental illness lasts,
      information about a place which induces the fear based mental illness, or
      information about a sound which induces the fear based mental illness, or
   wherein the at least one of the information about the object which induces the fear based mental illness, the information about a period during which the fear based mental illness lasts, the information about a place which induces the fear based mental illness, or information about the sound which induces the fear based mental illness is determined based on treatment intensity.

7. The method of claim 6, wherein the information about the object which induces the fear based mental illness comprises at least one of a number of instances of the object, a size of the object, a resolution of the object, a density of the object, and a distance to the object.

8. The method of claim 1, wherein the at least one of biometric information of the user comprises at least one of a heart rate, an electrocardiogram, a respiratory rate (RR), a blood pressure, a body temperature, a blood oxygen saturation, and a lactate level.

9. The method of claim 1, wherein the transmitting, to the electronic device, of the first control signal for the adjusting of the intensity of the treatment image comprises adjusting the treatment image based on diagnosis information that a medical professional generates based on the at least one of biometric information and the feedback information of the user during a predetermined period.

10. The method of claim 1, wherein the transmitting, to the electronic device, of the first control signal for the adjusting of the intensity of the treatment image comprises adjusting the intensity of the treatment image for the user who passes a predetermined criterion, based on treatment pattern information, the at least one of biometric information, and the feedback information of the user.

11. The method of claim 10, wherein the treatment pattern information comprises pattern information generated by using treatment data about a plurality of users of a certain treatment package.

12. The method of claim 1, wherein the transmitting, to the electronic device, of the first control signal for adjusting of the intensity of the treatment image comprises adjusting the intensity of the treatment image by applying a higher weight to the feedback information of the user than the at least one of biometric information.

13. The method of claim 1, wherein the
first biometric information is biometric information before a treatment event occurs, and the second biometric information is biometric information after the treatment event occurs.

14. The method of claim 1, wherein the determination to discontinue the treatment package comprises determining to discontinue the treatment package based on prior sign information.

15. The method of claim 1, wherein the determination to discontinue the treatment package comprises determining to discontinue the treatment package based on first threshold information generated by a medical professional or second threshold information generated based on treatment pattern information.

16. The method of claim 1, further comprising:
transmitting, to the electronic device, a control signal for executing a biofeedback package.

17. The method of claim 16, wherein the biofeedback package comprises a package configured to output the at least one of biometric information on the display of the electronic device via which the user checks the at least one of biometric information on the display so that the user controls a respiration.

18. A non-transitory computer-readable medium comprising computer-readable instructions to cause a computer to perform a method of comprising:
receiving a treatment request including authentication information of a user and a request for treating a fear based mental illness with which the user is diagnosed;
transmitting, to an electronic device of the user, a treatment package, including a treatment image, corresponding to the treatment request from among a plurality of treatment packages, based on the authentication information and the fear based mental illness, causing the treatment image to be output at an intensity based on the treatment package via a display of the electronic device;
receiving at least one of biometric information of the user and feedback information of the user based on a response from the electronic device of the user to the treatment image, wherein the at least one of biometric information includes a first biometric information and a second biometric information;
receiving a treatment intensity control signal based on the at least one of biometric information and the feedback information;
determining whether to continue the treatment package based on treatment pattern information, the at least one of biometric information, and the feedback information;
generating prior sign information based on an amount of change in the first biometric information and the second biometric information;
adjusting the intensity of the treatment image to be output based on the treatment pattern information, the at least one of biometric information, the feedback information, and the prior sign information;
transmitting, to the electronic device, a first control signal for adjusting an intensity of the treatment image, according to a determination to continue the treatment package; and
transmitting, to the electronic device, a second control signal for discontinuing a display of the treatment image, according to a determination to discontinue the treatment package,
wherein the adjusting of the intensity of the treatment image comprises changing a number of instances of an object within the treatment image based on the treatment pattern information, the at least one of biometric information, and the feedback information, changing a size of the object within the treatment image based on the treatment pattern information, the at least one of biometric information, and the feedback information, changing a resolution of the object within the treatment image based on the treatment pattern information, the at least one of biometric information, and the feedback information, changing a density of the object within the treatment image based on the treatment pattern information, the at least one of biometric information, and the feedback information, changing a proximity of the object within the treatment image based on the treatment pattern information, the at least one of biometric information, and the feedback information, and changing a duration of exposure to the object within the treatment image based on the treatment pattern information, the at least one of biometric information, and the feedback information.

19. A method of operating a user terminal for remote treatment of a fear based mental illness, the method comprising:
transmitting a treatment request including authentication information of a user and a request for treating the fear based mental illness with which the user is diagnosed;
receiving a treatment package, including a treatment image, corresponding to the treatment request from among a plurality of treatment packages, based on the authentication information and the fear based mental illness;
outputting the treatment image at an intensity via a display of an electronic device, or a display of a wearable device, based on the treatment package;
transmitting at least one of biometric information of the user and feedback information of the user based on a response from the electronic device of the user to the treatment image, wherein the at least one of biometric information includes a first biometric information and a second biometric information;
receiving treatment intensity control signal based on the at least one of biometric information and the feedback information a first control signal for adjusting of the intensity of the treatment image;
generating prior sign information based on an amount of change in the first biometric information and the second biometric information;
adjusting the intensity of the treatment image based on the treatment intensity control signal, the prior sign information, and according to a determination to continue the treatment package;
receiving a second control signal for discontinuing a display of the treatment image; and
discontinuing the display of the treatment image and executing a biofeedback package according to a determination to discontinue the treatment package,
wherein the receiving of the first control signal and the second control signal is based on determining whether to continue the treatment package according to treatment pattern information, the at least one of biometric information, and the feedback information, and
wherein the adjusting of the intensity of the treatment image comprises at least one of adjusting a number of instances of an object within the treatment image based on the treatment pattern information, the at least one of biometric information, and the feedback information, adjusting a size of the object within the treatment image based on the treatment pattern information, the at least one of biometric information, and the feedback information, adjusting a resolution of the object within the treatment image based on the treatment pattern information, the at least one of biometric information, and the feedback information, adjusting a density of the object within the treatment image based on the treatment pattern information, the at least one of biometric information, and the feedback information, adjusting a proximity of the object within the treatment image based on the treatment pattern information, the at least one of biometric information, and the feedback information, or adjusting a duration of exposure to the object within the treatment image based on the treatment pattern information, the at least one of biometric information, and the feedback information.

20. The method of claim 19,
wherein the electronic device comprises a first wearable device including a display and a second wearable device comprising a biometric sensor, and
wherein the first wearable device is separate from the second wearable device.

21. The method of claim 20, wherein the at least one of biometric information of the user is received from the second wearable device.

22. The method of claim 21, wherein the treatment request is generated by either the first wearable device or the second wearable device.

23. A server comprising:
a memory configured to store instructions; and
a processor, when executing the instructions, is configured to:
receive a treatment request including authentication information of a user and a request for treating a fear based mental illness with which the user is diagnosed,
transmit, to an electronic device of the user, a treatment package, including a treatment image, corresponding to the treatment request from among a plurality of treatment packages based on the authentication information and the fear based mental illness, causing the treatment image to be output at an intensity based on the treatment package via a display of the electronic device,
receive at least one of biometric information of the user and feedback information of the user based on a response from the electronic device of the user to the treatment image, wherein the at least one of biometric information includes a first biometric information and a second biometric information,
receive a treatment intensity control signal based on the at least one of biometric information and the feedback information,
determine whether to continue the treatment package based on treatment pattern information, the at least one of biometric information, and the feedback information,
generate prior sign information based on an amount of change in the first biometric information and the second biometric information,
adjust the intensity of the treatment image to be output based on the treatment pattern information, the at least one of biometric information, the feedback information, and the prior sign information,
transmit, to the electronic device, a first control signal for adjusting the intensity of the treatment image, according to a determination to continue the treatment package, and
transmit, to the electronic device, a second control signal for discontinuing the display of the treatment image, according to a determination to discontinue the treatment package,
wherein the adjusting of the intensity of the treatment image comprises at least one of adjusting a number of instances of an object within the treatment image based on the treatment pattern information, the at least one of biometric information, and the feedback information, adjusting a size of the object within the treatment image based on the treatment pattern information, the at least one of biometric information, and the feedback information, adjusting a resolution of the object within the treatment image based on the treatment pattern information, the at least one of biometric information, and the feedback information, adjusting a density of the object within the treatment image based on the treatment pattern information, the at least one of biometric information, and the feedback information, adjusting a proximity of the object within the treatment image based on the treatment pattern information, the at least one of biometric information, and the feedback information, or adjusting a duration of exposure to the object within the treatment image based on the treatment pattern information, the at least one of biometric information, and the feedback information.

\* \* \* \* \*